United States Patent [19]

Hooven

[11] Patent Number: 4,675,003
[45] Date of Patent: Jun. 23, 1987

[54] THREE STAGE PRESSURE REGULATOR VALVE

[75] Inventor: Michael D. Hooven, Miami, Fla.

[73] Assignee: Cordis Corporation, Miami, Fla.

[21] Appl. No.: 812,778

[22] Filed: Dec. 23, 1985

[51] Int. Cl.$^4$ .......................................... A61M 27/00
[52] U.S. Cl. ...................................... 604/9; 137/539; 604/247
[58] Field of Search ...................................... 604/8–10, 604/247; 137/504, 539

[56] References Cited

U.S. PATENT DOCUMENTS

| Re. 28,722 | 9/1960 | Whitacker | 137/508 |
|---|---|---|---|
| 79,436 | 6/1868 | Bechtel | 137/50 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander | 137/504 |
| 2,207,382 | 7/1940 | McNamara | 277/21 |
| 2,290,151 | 7/1942 | McCollum | 237/123 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Stuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,905,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,437,493 | 3/1984 | Okuda et al. | 138/45 |
| 4,443,214 | 4/1984 | Marion | 604/9 |
| 4,452,423 | 6/1984 | Bevlavi | 251/65 |

FOREIGN PATENT DOCUMENTS

| 702425 | 2/1941 | Fed. Rep. of Germany | 137/539 |
|---|---|---|---|
| 68509 | of 0000 | Netherlands . | |

Primary Examiner—Dalton L. Truluck
Attorney, Agent, or Firm—Lockwood, Alex, FitzGibbon & Cummings

[57] ABSTRACT

An implantable valve for allowing the passage of cerebrospinal fluid (CSF) from a ventricle of the brain to a suitable drainage location in the body includes a housing having an inlet and outlet with valving means in the housing to control fluid flow from the inlet to the outlet. The valving means includes various parts which are coaxially aligned between the inlet and outlet, the valving means having a valve seat, a valve closure means, a fluid flow restrictor means and a positioning means to control variable positioning of the valve closure means relative to the parts of the valving means. The valving means is actuable in response to applied pressure differentials, and regulates passage of CSF from the ventricular spaces to the drainage location. When the pressure differential is relatively small, the valve operates in a constant pressure mode to maintain a predetermined pressure differential across the valve. In response to a sudden increase in differential pressure, the valve operates in a constant flow mode to maintain a desired relatively constant CSF flow rate through the valve. Above a predetermined pressure differential, the valve operates in a constant pressure mode to maintain a predetermined maximum pressure differential across the valve.

9 Claims, 7 Drawing Figures

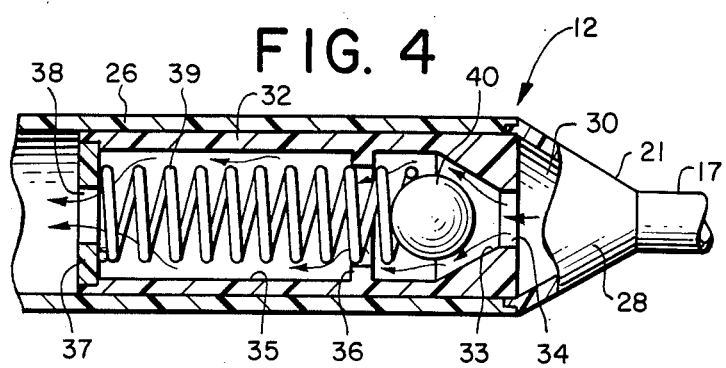
FIG. 4
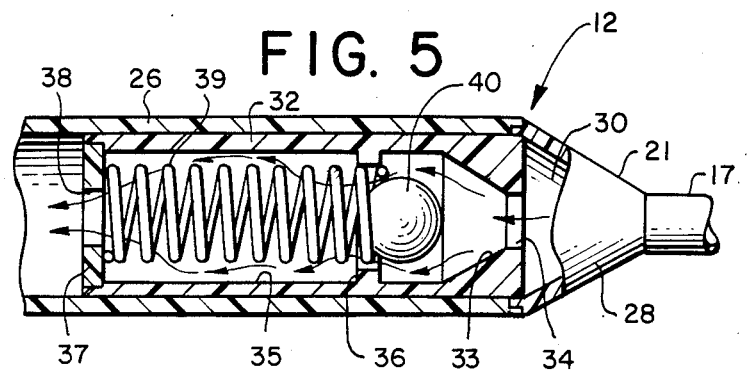
FIG. 5
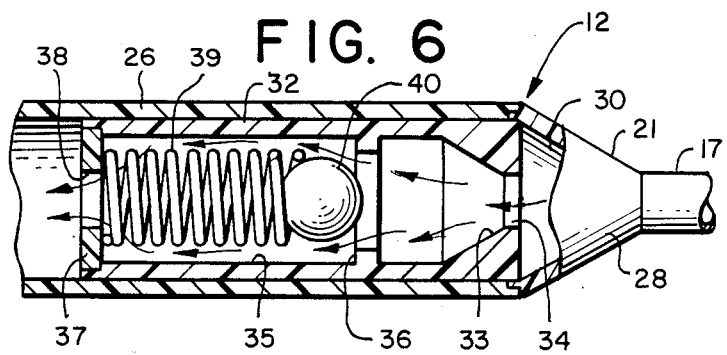
FIG. 6
FIG. 7
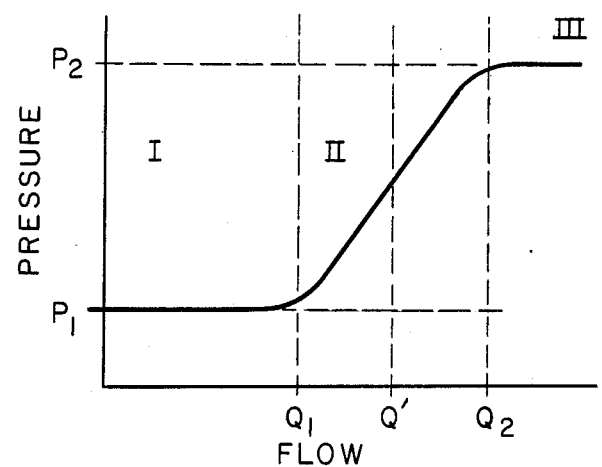

THREE STAGE PRESSURE REGULATOR VALVE

BACKGROUND OF THE INVENTION

The present invention relates to an intracranial pressure relief valve and, more particularly, to a simplified valve construction including coaxially aligned valve part members which establish three stage valve operation to provide either constant pressure or constant flow characteristics in accordance with a fluid pressure differential applied across the valve.

Hydrocephalus is a condition in which the body, for any one of a variety of reasons, is unable to relieve itself of excess cerebrospinal fluid (CSF) collected in the ventricles resulting in an abnormal increase in both epidural and intradural pressures. This in turn may cause a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. Accordingly, a variety of CSF pressure regulator valves and methods of controlling CSF pressure have been developed which include various check valves, servo valves or combinations thereof. Generally, such valves serve to divert CSF from the ventricles of the brain through a discharge line to some suitable drainage location in the body such as the venous system of the peritoneal cavity. Check valves operate by opening when the difference between CSF pressure and pressure in the discharge line exceeds a predetermined value.

The use of a simple check valve can be advantageous with respect to minimizing the cost of the valve, but with nothing more than check valve operation, the treatment of hydrocephalus is potentially disadvantageous since it is possible for such valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, resulting increased vertical height of the fluid column existing between the head and the selected drainage location may result in such an increase in differential pressure. Accordingly, valves, such as that described in the copending application of the present inventor, Ser. No. 672,868, filed Nov. 19, 1984, have been developed which serve to prevent undesired hyperdrainage by limiting the flow rate of fluid through the valve when a sudden increase in differential pressure occurs.

In this valve, a diaphragm, movable in response to the pressure differential between ventricular CSF pressure and pressure of fluids at the drainage location of the body, was mechanically coupled to a valve seat having a fluid metering orifice extending therethrough. The orifice allowed passage of CSF from the ventricular spaces to the selected drainage location. Motion of the diaphragm in response to change in the differential pressure caused the valve seat to be moved from a first position, in which the valve seat contacted a suitably located sphere to block and thereby prevent the passage of fluid through the orifice, to a second position, in which a generally cylindrical fluid flow restrictor partially occluded the orifice, thereby limiting fluid flow therethrough. By controlling the position of the sphere, the valve seat and the restrictor, it was possible to construct a valve having flow characteristics which avoided hyperdrainage with sudden changes in differential pressure.

As valves of this type are miniaturized, the number of parts involved, the complexity of the configurations of the various parts and the cost of generating the same become major factors. Working tolerances involved are on the order of 0.001 of an inch and continuing efforts are being made to reduce manufacturing costs while maintaining rather complex effective functioning.

The present invention is directed to an improvement in such a valve wherein the more standard types of valve elements or parts are utilized, the accumulated knowledge available in the manufacture of such parts being relied upon to reduce the cost of the valve. Basically, the preferred form of valve constructed in accordance with the present invention utilizes a sphere spring held against a valve seat somewhat similar to the well known type of check valve, the flow characteristics of the valve in response to variations in differential pressure being controlled by a restrictor element of simplified construction and cooperating with the check valve sphere in a unique manner to effectively provide the various modes of operation in the treatment of hydrocephalus.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which includes components which may be easily and economically manufactured.

It is a still more specific object of the present invention to provide a pressure regulator valve in which critically dimensioned components are of an easily manufactured configuration.

SUMMARY OF THE INVENTION

The invention is directed to a valve for controlling the passage of body fluids from one location in the body to another location. The valve includes a housing having first and second interior chamber areas. An inlet port establishes fluid communication between the first chamber area and the one location, while an outlet port establishes fluid communication between the second chamber area and the other location. A valve mechanism, including a series of coaxially aligned parts having a valve seat, valve seat closure means, fluid flow restrictor means and positioning means acting on the valve seat closure means, is actuable to a first condition in which fluid communication between the first and second chamber areas is prevented. The valve mechanism is also actuable to a second condition in which fluid communication is provided between the first and second chamber areas at a flow rate sufficient to maintain a substantially constant desired first pressure in the first chamber area, and to a third condition in which fluid communication is provided between the first and second chamber areas sufficient to maintain a desired substantially constant fluid flow rate. Finally, the valve mechanism is actuable to a fourth condition in which fluid communication is provided between the first and second chamber areas sufficient to maintain a substantially constant desired second pressure in the first chamber area. Thus, the valve sequentially prevents the passage of fluid between the one location and the other location, maintains a constant fluid pressure differential between the one location and the other location, maintains a desired constant rate of flow of fluid between the one location and the other location, and maintains a second constant desired fluid pressure differential between the one location and the other location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 4 is an enlarged cross-sectional view of the valve showing a section thereof and operation of the valve in a first constant pressure mode.

FIG. 5 is a cross-sectional view, similar to FIG. 4, showing the pressure relief valve in a constant flow rate mode.

FIG. 6 is a cross-sectional view, similar to FIG. 4, showing the pressure relief valve in a second constant pressure mode.

FIG. 7 is a graphical depiction of certain pressure and flow characteristics of the three stage pressure relief valve useful in understanding the operation thereof.

DESCRIPTION OF THE PREFERRED EMBODIMENT

Figure 1:
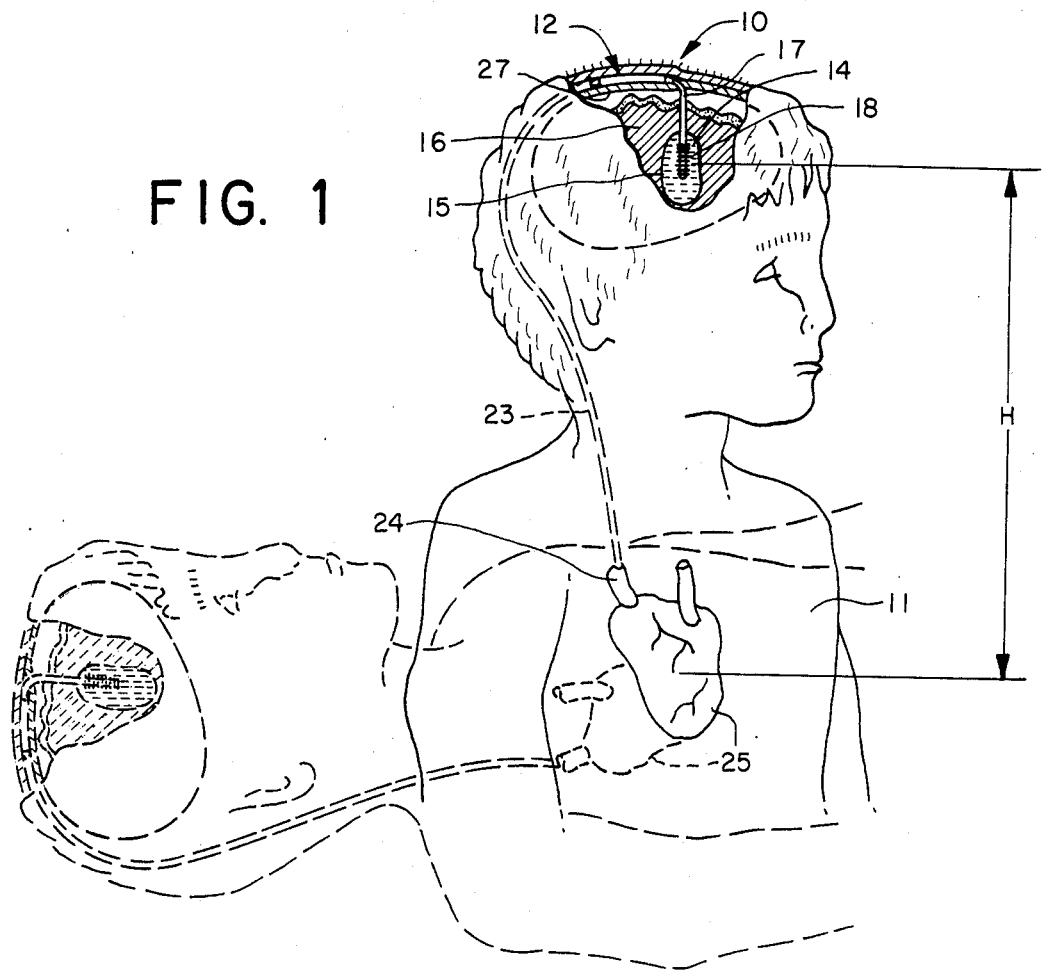
FIG. 1 is a perspective view, partially in section, of a CSF pressure relief system employing a three stage pressure regulator valve constructed in accordance with the present invention, showing such a system implanted within a patient.
Figure 2:
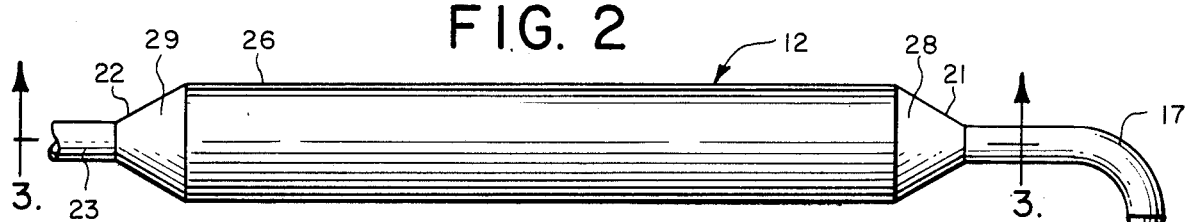
FIG. 2 is an elevational view of the pressure regulator valve.

Referring to the drawings, and particularly to FIGS. 1 and 2, a CSF pressure relief system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement within the brain. The distal end 18 of the catheter may be provided with a plurality of apertures 20 (FIG. 2) for allowing the passage of CSF therethrough and is positioned in a suitable brain ventricle 15. The other end of the catheter is coupled to the inlet port 21 of the valve to establish fluid communication between the valve and the ventricle. The outlet port 22 of the valve is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, pressure relief valve 12 allows passage of CSF from the brain ventricle to the selected discharge location to relieve excessive intracranial pressure caused by excessive accumulation of CSF.

While an increased differential pressure may result from the excessive accumulation of CSF in the brain ventricle, such an increase might also be a perfectly normal response to ordinary physical cavity of the patient. For example, when a patient stands after lying for some time in a recumbent position, as illustrated in phantom of FIG. 1, the differential pressure will suddenly increase by reason of the sudden increase in vertical height H of the fluid column existing between the distal end of the ventricular catheter 17 and the drainage location. If the relief valve were to open and permit unrestrained fluid flow in response to this pressure increase, hyperdrainage of the ventricle, and a brain hematoma, are possible results. Accordingly, the valve includes means for preventing such unrestricted fluid flow to the drainage location in the event of a sudden increase in the differential pressure.

Figure 3:
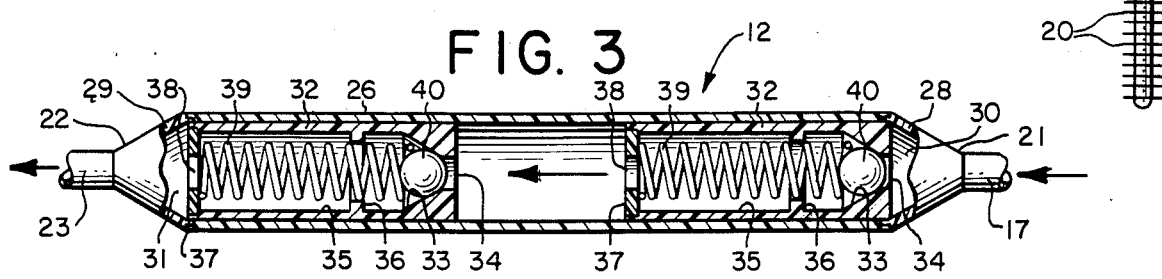
FIG. 3 is a cross-sectional view of the pressure regulator valve taken along line 3—3 of FIG. 2.

The construction of the three stage valve may best be understood by reference to FIGS. 2 and 3. As illustrated, the valve includes a tubular housing 26 fashioned from a durable, biologically compatible material, such as thermoplastic polymers of polyethersulfone or polycarbonates. The dimensions of the housing 26 are selected so as to be compatible with subcutaneous implantation of the valve over the cranium 27 (FIG. 1).

The housing 26 includes at opposite ends thereof frusto-conically shaped housing end members 28 and 29, which interiorly define chamber areas 30 and 31, respectively. Fluid flow through the valve is illustrated by the arrows forming apart of FIG. 3, the catheter 17 being attached to the inlet port 21 defined by the housing end member 28, and the catheter 23 being attached to the outlet port 22 defined by the housing end member 29.

Referring to FIG. 3, the interior of the housing 26 includes a pair of longitudinally spaced valve assemblies which are of identical construction. Each valve assembly includes a valve housing 32 formed from any suitable material such as stainless steel. At the inflow end of each valve assembly the housing is shaped to form a valve seat internally thereof, such seat being defined by the internal frusto-conical surface 33 which converges toward the inflow end of the housing and terminates in an annular orifice 34 defined by a flat inner surface. The divergent end of the seat 33 merges with an annular inner surface 35 of the valve housing 32, this inner surface being interrupted rearwardly of the valve seat in the direction of fluid flow by an inwardly projecting, annular fluid flow restrictor 36. The end of the valve housing 32 which defines the outlet end thereof is provided with an annular wall portion 37 or spring retainer having a centrally located fluid discharge orifice 38 therein. This end wall portion along the inner surface thereof surrounding the discharge orifice 38 establishes a seat for the adjacent end of a coil spring 39 which extends coaxially and centrally of the valve housing 32, through the restrictor ring 36 and into engagement with a valve seat closure member 40 which is in the form of a ball or sphere. The spring 39 is confined between the end wall portion 37 of the valve housing 32, this end wall portion functioning as a spring retainer, and the check valve sphere 40 which, in the absence of a predetermined fluid differential pressure, is held by the spring 39 in engagement with the valve seat 33 so as to occlude the fluid flow orifice 34.

The sphere 40 is highly polished and may be fabricated from synthetic sapphire. The spring 39 may be formed from stainless steel and is pre-calibrated so that the valve assembly will function in the manner to be described. The restrictor ring 36 is dimensioned to permit the spring and ball to move therethrough as will be described, the clearance being on the order of approximately 0.001 of an inch. Thus, the lumen of the valve housing 32 is restricted to a predetermined extend by the inwardly projecting annular ridge or ledge defining the restrictor 36.

While FIG. 3 illustrates the use of a pair of identical valve assemblies in the primary housing 26, it will be understood that single valve assembly may be utilized. Each of the valve assemblies illustrated in the embodiment of FIG. 3 functions is precisely the same manner as will be described. Briefly, the fluid discharge of the right hand valve assembly in FIG. 3 will exert the same pressure differential against the left hand valve assembly in FIG. 3, thus resulting in the same amount of fluid discharge therefrom. The provision of a pair of valve assemblies in the single main housing permits the total system to be tested after implantation. Pressure exerted on various points in the system, such as between the two valve assemblies of FIG. 3, can assist in determining whether blockage has occurred. To facilitate this testing, the primary housing 26 is flexible to some extent thereby permitting pressure to be applied to the housing between the valve assemblies after the system has been implanted. Application of appropriate pressure against the housing 26 between the valve assemblies will result in testing both valve assemblies. For example, depression of the central portion of the housing will increase the fluid pressure acting against the left hand valve assembly and will cause additional fluid flow therethrough. If by chance the right hand assembly is clogged to an extent that complete closure of the assembly is prevented, the centrally exerted pressure as described can assist in establishing this fact.

The various modes of operation of the three stage valve have been referred to hereinabove. FIG. 7 illustrates these modes. Basically, the pressure relief valve 12 normally operates to maintain a predetermined differential pressure $P_1$ between fluid in the brain ventricle and at the selected discharge location of the body. The valve accomplishes this by adjusting the fluid flow rate Q so that the pressure $P_1$ is maintained. This operation of the valve is shown in region I of FIG. 7.

When differential pressure rapidly increases, such as when the patient stands, a flow rate greater than a preselected rate $Q_1$ is necessary to maintain pressure $P_1$. However, such a flow rate may create the risk of undesirable hyperdrainage of the brain ventricle. Accordingly, when a rapid increase in differential pressure occurs, the valve automatically serves to maintain a relatively constant desired rate of fluid flow despite changes in differential pressure, as depicted in region II of FIG. 7. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 7. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve $Q_1$ and $Q_2$ might be 0.4 ml./min. and 0.8 ml./min., respectively, while first and second pressures, $P_1$ and $P_2$, may have values of 80 and 350 millimeters of water, respectively.

While it is desirable to avoid high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve. To avoid the possibility of building extremely high ventricular CSF pressure, the valve is constructed so that when differential pressure exceeds a predetermined pressure $P_2$ substantially higher than pressure $P_1$, the valve once again operates to allow a fluid flow rate sufficient to maintain a differential pressure no higher than pressure $P_2$. This operation is depicted in region III of FIG. 7. When the valve is operating in this region, further increases in differential pressure result in an increase in fluid flow through the valve thereby stabilizing differential pressure.

FIGS. 3 through 6 illustrate the four different conditions of fluid flow and/or valve assembly operation. Operation of a single valve assembly is illustrated in FIGS. 4 through 6. FIG. 3 shows the valve assembly in the first condition wherein fluid flow is prevented such as when differential pressure is negative or non-existent. As urged by the spring 39, the valve seat closure member 40 engages the frusto-conical ramp surface 33 of the valve seat and the fluid flow orifice 34 is completely closed. CSF fluid flow between chamber areas 30 and 31 is prevented.

When the differential pressure is relatively low, such as when the valve is operating in region I of FIG. 7, the resulting slight pressure is sufficient to displace the valve seat closure member 40 from the valve seat ramp 33 thereby allowing CSF to pass through the orifice 34 as shown in FIG. 4. The lumen of the restrictor 36 is sufficiently removed from the ball member 40 so as not be interfere with the flow of CSF between the chamber areas. Thus, the valve acts primarily as a constant pressure device whereby the pressure differential $P_1$ is maintained between the CSF in the chamber areas 30 and 31. A slight increase in differential pressure results in further movement of the ball member 40 against the action of the spring 39 thereby further opening the orifice 34 to allow greater CSF flow between the chamber areas. Similarly, a decrease in pressure allows the ball member 40 to move toward the valve seat ramp 33 restricting flow between the chamber areas and causing pressure in the chamber area 30 to increase.

FIG. 5 illustrates the operation of the valve when a sudden increase in differential pressure is applied to the valve. When such an event occurs, the pressure differential exceeds the predetermined regulated pressure $P_1$ and the valve operates in region II of FIG. 7. The displacement of the ball member 40 is now sufficient to bring the same into close association with the restrictor ring 36 so as to cause the ball member to move within the ring. Under these circumstances, the restrictor functions to partially occlude the fluid flow area within the valve housing 32. This increasing occlusion occurring by reason of increasing differential pressure is sufficient to offset the higher flow rate ordinarily resulting from increased pressure, resulting in a relatively uniform rate of fluid flow between the chamber areas despite such an increase in differential pressure. Accordingly, in this condition, the valve acts primarily as a constant flow device permitting the passage of fluid from chamber area 30 to chamber area 31 at a relatively constant predetermined rate despite changes in applied differential pressure.

FIG. 6 illustrates the operation of the valve in region III of FIG. 7, such as would occur when the differential pressure exceeds a predetermined pressure $P_2$. In this condition, differential pressure displaces the ball member 40 beyond the restrictor ring 36 so as to allow CSF to flow through the restrictor ring more readily by reason of reducing occlusion of the ring. The fluid flow area within the valve housing 32 is now less restricted than in region II. When the valve is operating in this manner, increases in differential pressure cause further opening of the valve and allows a greater fluid flow rate. Thus, the valve operates essentially as a constant pressure device whereby differential pressure greater than the predetermined maximum pressure $P_2$ is prevented.

The design of the valve mechanism of the present invention readily lends itself to miniaturization. The simplicity of construction enhances its usefulness while maintaining manufacturing cost at a minimum. Assembly of the valve is uncomplicated. These advantages plus the fact that the valve automatically provides control over multiple conditions of operation establishes the significance of the present invention.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A valve for controlling the passage of body fluids from a first location in the body to a second location, comprising:
   a bio-compatible housing having an interior passageway;
   inlet port means for establishing fluid communication between said interior passageway and the first location;
   outlet port means for establishing fluid communication between said interior passageway and the second location;
   valve closure means for providing a first valving mode in which fluid flow through said passageway is prevented in the absence of a first predetermined pressure differential between said inlet port means and said outlet port means;
   a first valving surface located along said interior passageway including, progressing from said inlet port means to said outlet port means, a first portion having a generally constant first diameter, a second portion having a generally constant second diameter less than said first diameter, and a third portion having a generally constant third diameter greater than said second diameter;
   a second valving surface being displaceable along the axis of said passageway in a direction away from said inlet port means in response to an increase in pressure differential between said inlet port means and said outlet port means thereby causing said second valving surface to successively coact with said first, second and third portions of said first valving surface to provide second, third and fourth valving modes, thereby in said second valving mode fluid flow occurs between said inlet port means and said outlet port means so as to maintain a first substantially constant predetermined pressure differential between said inlet port means and said outlet port means, in said third valving mode fluid flow remains substantially constant through said passageway notwithstanding changes in differential pressure between said inlet port means and said outlet port means, and in said fourth valving mode fluid flow occurs between said inlet port means and said outlet port means to maintain a second substantially constant predetermined pressure differential between said inlet port means and said outlet port means, said second pressure differential being greater than said first pressure differential.

2. The valve of claim 1 wherein said housing is tubular and said first valving surface and said second valving surface are substantially coaxial with the axis of said passageway.

3. The valve of claim 2 wherein said valve closure means includes a valve seat defining an orifice located adjacent to and in fluid communication with said passageway, said valve closure means further including a valve member which engages said valve seat to seal said passageway and urging means for urging said valve member towards said valve seat.

4. The valve of claim 3 wherein said valve member and said second valving surface are a ball valve member.

5. A valve for controlling the passage of body fluids from a first location in the body to a second location, comprising:
   a catheter means for removing a fluid from the first body location;
   drain means for discharging said fluid to the second location;
   a bio-compatible housing having first and second interior chambers in series fluid flow communication between said catheter means and said drain means;
   said first interior chamber having a first inlet opening for introducing said fluid from said catheter means into said first interior chamber and a first discharge opening for discharging said fluid from said first chamber;
   said first interior chamber having first valve means therein for regulating fluid flow through said first chamber, said first valve means including first valve closure means for preventing fluid flow through said first chamber in the absence of a first predetermined pressure differential between said first inlet opening and said first discharge opening, said first valve means also having a first valving surface located along said first interior chamber including, progressing from said first inlet opening to said first discharge opening, a first portion having a generally constant first diameter, a second portion having a generally constant second diameter less than said first diameter, and a third portion having a generally constant third diameter greater than said second diameter, a second valving surface being displaceable along the axis of said first chamber in a direction away from said first inlet opening in response to an increase in pressure differential between said first inlet opening and said first discharge opening to cause said second valving surface to successively coact with said first, second and third portions of said first valving surface to provide second, third and fourth valving modes;

said second interior chamber having a second inlet opening for introducing said fluid from said first discharge opening into said second interior chamber and a second discharge opening for discharging said fluid from said second chamber into said drain means;

said second interior chamber having second valve means therein for regulating fluid flow through said second chamber, said second valve means including second valve closure means for preventing fluid flow through said second chamber in the absence of said first predetermined pressure differential between said second inlet opening and said second discharge opening, said second valve means also having a third valving surface located along said second interior chamber including, progressing from said second inlet opening to said second discharge opening, a fourth portion having a generally constant fourth diameter, a fifth portion having a generally constant fifth diameter less than said fourth diameter, and a sixth portion having a generally constant sixth diameter greater than said fifth diameter, and a fourth valving surface being displaceable along the axis of said first chamber in a direction away from said second inlet opening in response to an increase in pressure differential between said second inlet opening and said second discharge opening to cause said fourth valving surface to successively coact with said fourth, fifth and sixth portions of said third valving surface to provide second, third and fourth valving modes;

whereby in said second valving mode fluid flow occurs between said catheter means and said drain means so as to maintain a first substantially constant predetermined pressure differential between said catheter means and said drain means, in said third valving mode fluid flow remains substantially constant through said first and second interior chambers notwithstanding changes in differential pressure between said catheter means and said drain means, and in said fourth valving mode fluid flow occurs between said catheter means and said drain means to maintain a second substantially constant predetermined pressure differential between said catheter means and said drain means, said second pressure differential being greater than said first pressure differential.

6. The valve of claim 5 wherein a portion of said housing located between said first and second interior chamber includes a flexible area for operational testing of the valve.

7. The valve of claim 6 wherein said housing is tubular.

8. The valve of claim 7 wherein said first valving surface, said second valving surface, said third valving surface, said fourth valving surface, the axis of said first chamber and the axis of said second chamber are all substantially coaxially aligned.

9. The valve of claim 8 wherein said first and second valve closure means include a valve seat, a valve member which engages said valve seat to seal each said chamber and urging means for urging said valve member towards said valve seat.

* * * * *